United States Patent [19]

Hale

[11] Patent Number: 5,313,819
[45] Date of Patent: May 24, 1994

[54] QUANTIFICATION OF BLAST FURNACE SLAG IN A SLURRY

[75] Inventor: Arthur H. Hale, Houston, Tex.

[73] Assignee: Shell Oil Company, Houston, Tex.

[21] Appl. No.: 15,204

[22] Filed: Feb. 10, 1993

[51] Int. Cl.$^5$ .............................................. G01N 7/00
[52] U.S. Cl. ................................... 73/19.01; 73/23.2; 73/61.41
[58] Field of Search ................... 73/61.41, 19.01, 23.2; 436/120, 121, 177

[56] References Cited

U.S. PATENT DOCUMENTS

| | | | |
|---|---|---|---|
| 4,661,459 | 4/1987 | Hirtz | 73/19.01 |
| 4,740,473 | 4/1988 | Tomlin | 436/120 |
| 4,977,093 | 12/1990 | Cooke | 436/120 |
| 4,997,768 | 3/1991 | Uffenheimer et al. | 436/177 |
| 5,010,022 | 4/1991 | Lindstrom | 436/120 |
| 5,049,508 | 9/1991 | Hilscher et al. | 436/121 |

*Primary Examiner*—Hezron E. Williams
*Assistant Examiner*—Valerie D. Francies

[57] ABSTRACT

A method to determine the amount of blast furnace slag in a slurry sample. The slurry is preferably a drilling fluid or a wellbore cement slurry. The method comprises correlating the amount of hydrogen sulfide released from acidified slurries with the amount of blast furnace slag in the slurry and acidifying the sample and determining the amount of hydrogen sulfide released from the acidified sample.

9 Claims, No Drawings

QUANTIFICATION OF BLAST FURNACE SLAG IN A SLURRY

FIELD OF THE INVENTION

The present invention relates to a method to determine the amount of blast furnace slag in a sample.

BACKGROUND OF THE INVENTION

Tragesser, in U.S. Pat. No. 3,557,876 and Nahm in U.S. patent application Ser. No. 691,905, disclose the addition of pozzolana to drilling fluids. These pozzolanas, when included in drilling fluids, provide a filter cake to prevent fluid loss from the wellbore wherein the filter cake has certain desirable properties. The filter cakes deposited from pozzolana-containing drilling muds can be made to be compatible with cements, and the filter cake itself can be converted into a cementitious material that bonds well with both wellbore cement and the formation. This eliminates problems of contamination of cement by incompatible filter cakes, and eliminates the need to displace mud and filter cake prior to cementing. Pozzolana, according to Tragesser, includes fly ash, flue dust, certain boiler and furnace slags, burnt ground brick, by-products of certain industrial processes, pumicites or volcanic ashes, pumice or pumice stones, obsidian, scoria, tuffs, some of the andesites, diatomites, cherts, shale, clays and pure opal. Nahm discloses particular advantages for the use of blast furnace slag as the pozzolan.

An improvement to the methods of using pozzolan-containing drilling muds is to convert the pozzolan-containing drilling muds directly to cementing slurries. Converting drilling muds directly to cementing slurries eliminates the need to dispose of used muds, eliminates the need to add some materials to the cement that are already present in the muds, such as fluid loss additives, and further improves compatibility of the muds with cementing slurries. Mud-based cements such as these are disclosed in U.S. Pat. Nos. 3,168,139; 3,499,491; and 5,058,679. U.S. Pat. No. 5,058,679 discloses a conversion of drilling mud directly to a cement slurry by adding blast furnace slag; curing agents such as sodium hydroxide, potassium hydroxide, zinc carbonate, or sodium carbonate; and optionally set control additives. The use of blast furnace slag cements instead of Portland cements significantly lowers cement costs, and further improves compatibility with pozzolan-containing drilling muds.

Determination of the amount of blast furnace slag in the drilling mud and in the cement slurry becomes particularly important when blast furnace slag containing drilling mud is converted to blast furnace slag cement or when blast furnace slag containing drilling fluids are used to obtain a settable filter cake. The amount of blast furnace slag remaining in mud will vary depending upon many factors. The amount of blast furnace slag in a final cementing slurry or a recycled drilling mud must be controlled to accomplish an acceptable slurry rheology, set time, and set cement properties.

U.S. patent application Ser. No. 964,981 addresses the need to determine quantitatively the amount of blast furnace slag in a slurry such as a drilling fluid or a cement slurry. This patent provides a method whereby a sample of slurry is annealed to convert the blast furnace slag into crystalline forms that can be quantitatively determined by conventional X-ray diffraction techniques. This method is useful, but it requires a considerable amount of time and requires relatively expensive X-ray diffraction equipment. There remains a need for a quick and simple quantitative test for blast furnace slag in slurries that can be quickly performed at a drilling site.

It is therefore an object of the present invention to provide an analytical method capable of determining the amount of blast furnace slag in slurries such as cement slurries, drilling muds, completion fluids, and workover fluids. It is further object to provide such a method that is simple and can be performed at a drilling site.

SUMMARY OF THE INVENTION

These and other objects are accomplished by a method to determine the concentration of blast furnace slag in a slurry comprising the steps of: providing a slurry sample; acidifying the slurry sample; determining the concentration of sulfides in the acidified sample; correlating the concentration of blast furnace slag in a slurry such as the sample with concentration of sulfide in an acidified slurry such as the acidified sample; and determining based on the correlation of concentration of blast furnace slag with the concentration of sulfides in the acidified sample, and the concentration of sulfides in the acidified sample, the concentration of blast furnace slag in the sample.

This method can be performed at drilling sites or other remote locations because skilled technicians are not required to perform this test. This method also does not require complicated equipment. The results of this method are acceptably reproducible for most field control of blast furnace slag additions.

The amount of blast furnace slag in the sample can be correlated to the amount of sulfide in the acidified sample by either adding known amounts of slag to a slurry and measuring sulfides according to the method of determining sulfides of the present invention, or the amount of slag in the slurry may be determined by an independent method such as the method disclosed in U.S. patent application Ser. No. 964,981 to calibrate the present method.

DETAILED DESCRIPTION OF THE INVENTION

The slurry samples of the present invention are preferably slurry samples of blast furnace slag containing drilling fluids or blast furnace slag containing cement slurries. Other slurries containing blast furnace slag could also be tested for blast furnace slag content according to the present invention. The slurry sample of the present invention should be relatively free of sulfides from sources other than the blast furnace slag. Preferably, sulfides other than from slag are less than about 100 ppm. Thus, if the slurry is a drilling fluid, and the drilling fluid has contacted a formation containing significant amounts of hydrogen sulfide, the present invention would render erroneously high blast furnace slag content results if the hydrogen sulfide originating in the formation is not taken into account. Even if a formation contains hydrogen sulfides, when a proper over-balanced pressure is maintained in the wellbore, the present invention can still be useful in determining the blast furnace slag content of the drilling mud without further modification. When drilling fluids are contaminated with hydrogen sulfide the blast furnace slag content of the slurry may be determined by adding incremental amounts of blast furnace slag to the slurry sample to determine a correlation of blast furnace slag to sulfides in that slurry. In this case, the contaminating hydrogen sulfides result in a "high baseline" of sulfides at a zero blast furnace slag concentration. Alternatively, because the sulfides are insoluble under normal drilling conditions (i.e., prior to acidification), sulfides from the blast furnace slag are not present in filtrate when the slurry sample is filtered (Whatman 50 paper, API filter press). A slurry sample can therefore be filtered, and a new slurry constituted from the filtered solids that contains the blast furnace slag of the original sample without any contaminating hydrogen sulfide.

Slurry samples containing from about one to about 60 lb/bbl of blast furnace slag are preferred in the practice of the present invention. Samples containing about 60 to about 200 lb/bbl of blast furnace slag are preferably diluted about 1:1 with a distilled water prior to determining the blast furnace slag content. Samples containing about 200 to about 400 lb/bbl of blast furnace slag are preferably diluted by a ratio of about 1:3 of slag to water in order for the sulfides content and sample viscosities to be in ranges that are readily measured by the present invention. Higher concentrations of blast furnace slag may simply by diluted further.

Sulfides in the sample of slurry may be determined by any convenient method although the method of API RP 13B, Recommended Practice Standard Procedure for Field Testing Drilling Fluids, is preferred. This test is acceptably accurate, and very simple to perform. Soluble sulfides are measured by this test. Soluble sulfide include $H_2S$, and the sulfide ($S^{-2}$) and bisulfide ($HS^-$) ions. A Garrett Gas Train apparatus is utilized in the API RP 13B method. The Garrett Gas Train provides chambers through which gas can be bubbled through a liquid sample separated from the sample, and then passed through a Dräger tube. The procedure, as described in API RP 13B and modified as necessary to measure sulfides in a slurry, is as follows:

a. Be sure the gas train is clean, dry and on a level surface with the top removed.
b. Add 20 cm³ of deionized water to Chamber 1.
c. Add 5 drops of octanol defoamer to Chamber 1.
d. Select the proper type Dräger tube for the sample volume and the expected sulfide range. Break the tip from each end of the Dräger tube.
e. Install the Dräger tube with the arrow pointing downward into the bored receptacle of the Garrett Gas Train. Likewise, install the flowmeter tube with the word TOP upward. Be sure o-rings seal around the body of each tube.
f. Add to Chamber 1 about 10 cm³ of slurry that has been diluted with about one part water per part of slurry.
g. Install the top on the gas train and hand tighten all screws evenly to seal the o-rings.
h. With the regulator backed off, using flexible tubing connect a supply of an inert carrier gas to the dispersion tube of Chamber 1. If a $CO_2$ cartridge is used, install and puncture cartridge and connect to dispersion tube.
i. Attach the flexible tubing from Chamber 3 outlet to the Dräger tube.
j. Adjust the dispersion tube in Chamber 1 to approximately ¼ in. (5 mm) above the bottom.
k. Gently flow carrier gas for a 30 second period to purge air from the system. Check for leaks. Shut off the carrier gas.
l. Slowly inject 10 cm³ of 5N sulfuric acid solution into Chamber 1 through rubber septum using the hypodermic syringe and needle.
m. Immediately restart the carrier gas flow. The flow rate should be maintained between 200–400 cm³ per minute.
n. Observe the changes in appearance of the Dräger tube. Note and record the maximum darkened length (in units marked on the tube) before the darkened front starts to smear. Continue flowing for a total of 15 minutes although the darkened front may attain a diffuse and feathery coloration. In high-range Dräger tubes an orange color (caused by $SO^2$) may appear ahead of the black front if sulfites are present in the sample. The orange $SO_2$ region should be ignored when recording darkened length.
o. A lead-acetate paper disk fitted under the o-ring of Chamber 3 can be substituted for the Dräger tube in the Gas Train. The lead-acetate paper will show qualitatively the presence or absence of sulfides in the sample. A dark discoloration of the paper is a positive indication of sulfides. After the positive indication, the Dräger tube should be used on a separate sample for quantitative analysis.
p. To clean the gas train remove the flexible tubing and remove the top. Take Dräger tube and flowmeter out of the receptacles and plug the hole with stoppers to keep them dry. Wash out the chambers with warm water and mild detergent, using a soft brush. Use a pipe cleaner to clean the passages between the chambers. Wash, rinse, and blow out the dispersion tube with a dry gas. Rinse the unit with deionized water and allow to drain dry.
q. Calculate the amount of sulfides in the slurry sample as follows:

Using the measured Sample Volume, the Dräger tube's maximum Darkened Length and the Tube Factor, calculate sulfide in the sample:

$$\text{Sulfide, mg/L} = \frac{\text{(Darkened Length*)(Tube Factor)}}{\text{(Sample Volume, cm}^3\text{)}}$$

The procedure of API RP 13B calls for a solid-free filtrate sample to be syringed into the gas train chamber with a hypodermic syringe and needle. These aspects of API RP 13B are modified to permit sampling of the slurry.

A filtrate of a blast furnace slag slurry before acidification will not have a significant sulfides content. The acidification of the blast furnace slag solids releases sulfides from the solids, and this hydrogen sulfide is released in an amount that is proportional to the amount of blast furnace slag in the slurry. It could therefore be expected that blast furnace slag from different sources or of different particle sizes will result in somewhat different amounts of sulfides being released from each gram of blast furnace slag in the slurry sample. Correlation of the amount of blast furnace slag in the sample with the amount of sulfide in an acidified sample is therefore a critical step in the practice of the present invention. This correlation can be made, for example, by preparation of slurries of known amounts of similar blast furnace slags in either water or carrier fluid similar to the carrier fluids of the slurry in which the concentration of the blast furnace slag is to be determined, and determination of the amounts of blast furnace slag in the slurry. Alternatively, increments of blast furnace slag have been added to the slurry for which the blast furnace slag content is to be determined. When increments of blast furnace slag are added to the slurry, the amount of blast furnace slag in the original slurry is determined by assuming that the slurry without blast furnace slag has no sulfide in the acidified slurry. A third method to correlate the concentration of blast furnace slag in the sample with concentration of sulfides in an acidified sample of slurry is to determine the correlation from data such as that given in the Example of this specification, and neglecting any differences between the slurries or blast furnace slags. Another method to arrive at such a correlation is to determine the amount of blast furnace slag in a sample by a method such as that taught in U.S. patent application Ser. No. 964,981 and determine the amount of sulfides in an acidified slurry sample using a Garrett Gas Train, and assume that the sulfides vary proportionately with the slag concentration.

The blast furnace slag containing slurry is preferably diluted to enable intimate contact between the inert carrier gas and the sample when a Garrett Gas Train is used. This intimate contact is beneficial because it enables removal of hydrogen sulfide by the carrier gas in a reasonable amount of time. Dilution can therefore be beneficial if the initial slurry is too viscous for intimate contact between the carrier fluid and the carrier gas. Dilution to a viscosity that permits intimate contact between the inert carrier gas and the diluted slurry is preferred.

Acidification of the slurry sample is required for the blast furnace slag solids to convert various sulfides to hydrogen sulfide. A large excess of a strong acid is preferred although enough acid of any kind sufficient to decrease the pH of the blast furnace slag slurry to about two or less will be sufficient. Hydrogen sulfide is considerably less soluble in low pH solutions, so the acidification also enhances the removal of hydrogen sulfides from the acidified slurry in an apparatus such as the Garrett Gas Train.

EXAMPLE

Samples of slurries containing blast furnace slag were prepared by adding to 350 ml portions of a 20% by weight NaCl drilling mud containing partially hydrolyzed polyacrylamide (PHPA) and enough slag to result in the concentration of the slag in the mud indicated below in Table 1. The drilling mud was obtained from the drilling of a Gulf of Mexico well. Glucoheptonate was added to the slurries in an amount of one percent by weight based on the blast furnace slag to retard setting of the blast furnace slag. The concentration of blast furnace slag varied from 0 to 100 lb/bbl. The samples were hot rolled at 150° F. for 16 hours to thoroughly mix the slurries. The samples were then diluted by an equal volume of fresh water.

About 10 cm$^3$ of each sample was acidified with about 10 cm$^3$ of 5N sulfuric acid solution and the sulfides in the acidified sample were determined in a Garrett Gas Train as described above. The resultant sulfide concentrations are listed in Table 1 based on the original slurry samples. The amount of sulfide in the sample was correlated to the amount of slag in the samples by least squares. The resultant correlation is:

$$Sulfides(ppm) = 80 + 12.22 \times (lb\ slag/bbl\ slurry) \qquad (1)$$

Table 1 includes a "predicted sulfides" which is the amount of sulfides that would be predicted to be in the slurry based on the amount of slag and equation 1.

TABLE 1

| Slag (lb/bbl) | H$_2$S (ppm) | Predicted H$_2$S (ppm) |
|---|---|---|
| 0 | 20 | 80 |
| 10 | 222 | 202 |
| 20 | 300 | 324 |
| 30 | 480 | 447 |
| 50 | 750 | 691 |
| 70 | 1110 | 935 |
| 100 | 1140 | 1302 |

This example demonstrates that the amount of a particular blast furnace slag in a blast furnace slag slurry varies linearly with the amount of sulfides generated by acidification of that slurry such that the amount of blast furnace slag in a slurry may be determined to within a reasonable accuracy by determination of the sulfides in such a slurry after acidification. As can be seen from Table 1, the linearity of the sulfides versus slag content function decreases at greater slag concentrations. This is most likely caused by the increasing viscosity of the slurry. It would therefore be preferable to dilute the slurries with more fresh water at slag concentrations higher than about 80 lb/bbl. A ratio of slurry to dilution water of 1:4 or more may be desirable if the slurry contains 80 lb/bbl of blast furnace slag or more.

The foregoing example is exemplary and attached claims define the scope of the present invention.

I claim:

1. A method to determine the concentration of blast furnace slag in a slurry sample comprising the steps of:
   acidifying the slurry sample;
   determining the concentration of sulfides in the acidified sample;
   establishing a correlation between the concentration of blast furnace slag in the slurry and the concentration of sulfide in the acidified slurry; and
   determining, based on the correlation of concentration of blast furnace slag with the concentration of sulfides in the acidified slurry, the concentration of blast furnace slag in the sample.

2. The method of claim 1 wherein the step of determining the concentration of sulfides in the acidified sample; is conducted by passing a known volume of inert gas through the acidified sample; and determining the amount of sulfides the inert gas.

3. The method of claim 2 wherein the step of establishing a correlation between the amount of blast furnace slag with the amount of sulfide in the acidified slurry is conducted by determining said sulfide concentration from said inert gas wherein said inert gas is passed through a slurry having a known amount of blast furnace slag added to a slurry free of blast furnace slag.

4. The method of claim 3 wherein said correlation is established by determining said sulfide concentration rom more than one slurry; each of said slurries having different known amounts of blast furnace slag added to a slurry free of blast furnace slag.

5. The method of claim 1 further comprising the step of diluting the slurry sample with water by a ratio of slurry sample to water of at least 1:1.

6. The method of claim 2 wherein a defoamer is added to the slurry sample before the inert gas is passed through the acidified slurry sample.

7. The method of claim 8 wherein the inert gas is selected from the group of inert gases consisting of carbon dioxide and nitrogen.

8. The method of claim 5 wherein the slurry sample is diluted by at ratio of slurry sample to water of at least about 1:4.

9. The method of claim 1 wherein the slurry sample contains between about 1 and 60 pounds of blast furnace slag per barrel of slurry sample.

* * * * *